United States Patent [19]
Yamazaki et al.

[11] 3,953,514
[45] Apr. 27, 1976

[54] PROCESS FOR PREPARING CYCLOPENTENONE DERIVATIVES

[75] Inventors: Toshiharu Yamazaki; Mamoru Nakai; Yoshiaki Kuroki, all of Ube, Japan

[73] Assignee: Ube Industries, Ltd., Ube, Japan

[22] Filed: Aug. 12, 1974

[21] Appl. No.: 496,755

[30] Foreign Application Priority Data
Aug. 31, 1973  Japan................................ 48-97349

[52] U.S. Cl........................... 260/586 C; 260/586 G
[51] Int. Cl.² ................... C07C 45/00; C07C 45/18
[58] Field of Search ................................ 260/586 C

[56] References Cited
OTHER PUBLICATIONS
Frank et al., "J. Am. Chem. Soc.," Vol. 70, pp. 1379–1381 (1948).
Dev, "Chem. Abstracts", Vol. 52, pp. 1996–1997 (1958).
Abramenko et al., "Chem. Abstracts", Vol. 60, p. 4028a (1964).
Patnekar et al., "Chem. Abstracts," Vol. 64, p. 17643c (1966).

*Primary Examiner*—Norman Morgenstern
*Attorney, Agent, or Firm*—Flynn & Frishauf

[57] ABSTRACT

A novel and industrial process for preparing cyclopentenone derivatives by heating $C_5 \sim C_{13}$ aliphatic acids having one substituent or intramolecular esters thereof in the presence of a solid acid catalyst in a good yield.

10 Claims, No Drawings

PROCESS FOR PREPARING CYCLOPENTENONE DERIVATIVES

This invention relates to a novel process for preparing cyclopentenone derivatives.

More particularly, it relates to a process for preparing cyclopentenone derivatives which comprises heating an aliphatic acid containing 5 to 13 carbon atoms and having one substituent selected from a halogen atom and hydroxyl, alkoxyl and acyloxyl radicals in any one position of $\gamma$-, $\delta$-, $\epsilon$- or $\omega$-position or an intramolecular ester thereof in the presence of a solid acid catalyst.

Cyclopentenone derivatives have various uses as starting materials for several medicaments, perfumes and agricultural chemicals. But in spite of the above many uses, few industrial preparations of cyclopentenone derivatives have been found.

Among the known methods for preparing cyclopentenone derivatives, there is a process for preparing cyclopentenone derivatives by heating $\gamma$-lactone in liquid phase with phosphorus pentoxide (J. Am. Chem. Soc., 70, 1379 (1948)). But this process has such defects in that although it needs a large amount of phosphorus pentoxide (more than an equi-molecular amount of $\gamma$-lactone used), the yield of cyclopentenone derivatives is very low and isolation and purification of the object compound from the reaction product are very complicated. Further, this process affords little cyclopentenone derivatives in cases where simple structural lactone compounds, for example, $\gamma$-caprolactone or $\gamma$-dimethyl-$\gamma$-butyrolactone are used as starting materials.

There is known another analogous method which comprises heating $\gamma$-lactones in a mixture of phosphorus pentoxide and phosphoric acid at a temperature of about 100°C under stirring (Chem. Abst., 52 1977 (1958)). But even in this method the above defects have hardly been improved.

Therefore, the present inventors have attempted an extensive study for obtaining an industrial and useful method for the preparation of cyclopentenone derivatives and found that cyclopentenone derivatives can be prepared economically in a good yield by heating a $C_5 \sim C_{13}$ aliphatic acid having one substituent selected from a halogen atom and hydroxyl, alkoxyl and acyloxyl radicals in any one position of $\gamma$-, $\delta$-, $\epsilon$- or $\omega$-position or an intramolecular ester thereof in the presence of a solid acid catalyst.

Therefore, an object of this invention is to provide a novel process for preparing cyclopentenone derivatives.

Another object of this invention is to provide an industrial and economical process for preparing cyclopentenone derivatives.

A still another object is to provide a process for preparing cyclopentenone derivatives in a good yield.

All other objects of this invention will be apparent from the disclosure and appended claims.

This invention will be described in detail as follows.

Among the aliphatic acids used as starting materials according to this invention, as the examples of straight aliphatic acids there may be mentioned $\epsilon$-methoxycaproic acid, $\delta$-bromocaproic acid, $\omega$-chloroheptanoic acid, $\gamma$-methoxyheptanoic acid, $\gamma$-methoxycaprylic acid, $\delta$-propoxypelargonic acid, $\epsilon$-methoxypelargonic acid, $\gamma$-methoxycapric acid, $\delta$-methoxycapric acid, $\epsilon$-chlorocapric acid, $\delta$-methoxyundecylenic acid, $\gamma$-bromolauric acid, $\gamma$-chlorotridecylic acid, and $\delta$-bromotridecylic acid. As examples of branched aliphatic acids there may be mentioned $\gamma$-methyl-$\epsilon$-chlorocaproic acid, $\gamma$-methyl-$\epsilon$-acetoxycaproic acid, $\gamma$-methyl-$\epsilon$-hydroxycaproic acid, $\gamma$-methyl-$\gamma$-methoxycaproic acid, $\gamma$-methyl-$\delta$-propoxyheptanoic acid, $\gamma$-methyl-$\epsilon$-hydroxyheptanoic acid, $\gamma$-methyl-$\gamma$-chlorocaprylic acid, $\gamma$-methyl-$\epsilon$-bromocaprylic acid, $\gamma$-methyl-$\gamma$-methoxypelargonic acid, $\gamma$-methyl-$\omega$-chloropelargonic acid, $\gamma$-methyl-$\gamma$-bromopelargonic acid, $\gamma$-ethyl-$\delta$-acetoxypelargonic acid, $\gamma$-methyl-$\omega$-methoxycapric acid, $\gamma$-ethyl-$\delta$-chlorocapric acid, $\gamma$-methyl-$\gamma$-chlorocapric acid, $\gamma$-ethyl-$\delta$-hydroxycapric acid, $\gamma$-methyl-$\delta$-chloroundecylenic acid, $\gamma$-methyl-$\delta$-methoxylauric acid. Also, intramolecular esters can be easily prepared by heating the above aliphatic acids in the presence of an acid or a base. As examples of these esters, there may be mentioned $\gamma$-dimethyl-$\gamma$-butyrolactone, $\gamma,\gamma$-undecamethylene-$\gamma$-butyrolactone, $\gamma$- or $\delta$-valerolactone, $\gamma$-methyl-$\delta$-valerolactone, $\gamma$-, $\delta$- or $\epsilon$-caprolactone, $\gamma$-methyl-$\gamma$-, $\delta$- or $\epsilon$-caprolactone, $\gamma$-, $\delta$- or $\epsilon$-enantholactone, $\gamma$-methyl-$\gamma$-, $\delta$- or $\epsilon$-enantholactone, $\gamma$-, $\delta$- or $\epsilon$-caprylolactone, $\gamma$-methyl-$\gamma$-, $\delta$- or $\epsilon$-caprylolactone, $\gamma$-, $\delta$- or $\epsilon$-pelargolactone, $\gamma$-methyl-$\gamma$-, $\delta$- or $\epsilon$-pelargolactone, $\gamma$-, $\delta$- or $\epsilon$-decalactone, $\gamma$-methyl-$\gamma$-, $\delta$- or $\epsilon$-decalactone, $\gamma$-, $\delta$- or $\epsilon$-undecalactone, $\gamma$-methyl-$\gamma$-, $\delta$- or $\epsilon$-undecalactone.

According to this invention these aliphatic acids or intramolecular esters thereof may be used in liquid or gaseous state. As examples of solid acid catalysts used in the process of this invention there are mentioned oxides such as silica-alumina, silica-magnesia, silica-boria, alumina-boria, and silica-titania, phosphates such as sodium phosphate, calcium phosphate, magnesium phosphate, boron phosphate, zirconium phosphate and titanium phosphate, or solid phosphoric acid and a mixture of the said compounds. Among the above catalysts, the phosphates and solid phosphoric acid may be used in a form supported on silica gel, alumina or diatomaceous earth. Sulphates such as nickel sulphate, zinc sulfate, calcium sulphate, manganese sulfate, copper sulfate, cobalt sulfate, cadmium sulfate, strontium sulfate, magnesium sulfate, ferric sulfate, barium sulfate, potassium hydrogen sulfate, potassium sulfate and aluminium sulfate, chromium oxide or a mixture of these compounds are also useful in a form supported on silica gel, alumina, or diatomaceous earth. Further, solid acid catalysts such as silica-alumina, silica-magnesia and silica-titania which are of strong acidity are preferred to be used, if desired, in a state poisoned with alkali. These solid acid catalysts can be manufactured in a known conventional procedure and for facilitating of taking the product out from the reaction vessel containing the catalyst layer. Optionally introduction of an inert gas such as nitrogen gas into the reaction vessel is preferred.

According to this invention, the heating temperature of aliphatic acids or intramolecular esters thereof in the presence of solid acid catalysts is a temperature of from 200° to 500°C, most preferably from 300° to 450°C, because the yield of cyclopentenone derivatives decreases at a temperature of under 200°C and side reactions such as evolution of lower hydrocarbons and carbon dioxide through thermal decomposition occur at a temperature of above 500°C.

As examples of cyclopentenone derivatives obtained by this invention there are mentioned 2-cyclopentenone, 2-methyl-2-cyclopentenone, 3-methyl-2-cyclopentenone, 2-methyl-3-methyl-2-cyclopentenone, 2-ethyl-2-cyclopentenone, 2-ethyl-3-methyl-2-cyclopentenone, 2-propyl-2-cyclopentenone, 2-propyl-3-methyl-2-cyclopentenone, 2-butyl-2-cyclopentenone, 2-butyl-3-methyl-2-cyclopentenone, 2-pentyl-2-cyclopentenone, 2-pentyl-3-methyl-2-cyclopentenone, 13-ketobicyclo[10,3,0]-1(12)-pentadecene.

As methods for recovering cyclopentenone derivatives from a mixture containing by-products and the unreacted aliphatic acids or intramolecular esters according to this invention, known conventional methods such as distillation, solvent extraction, recrystallization and gas chromatography are optionally applied.

According to this invention, even in case of using $C_5 \sim C_{13}$ aliphatic acids having one substituent selected from a halogen atom and hydroxyl, alkoxyl and acyloxyl radicals in any one position of $\gamma$-, $\delta$-, $\epsilon$- or $\omega$-position or intermolecular esters thereof other than those used in the Examples and of using solid acid catalysts other than those used in the Examples, cyclopentenone derivatives can be obtained in the same good yield as in each Example. The results of the Examples and Comparative Example show that cyclopentenone derivatives can be prepared by the process of this invention more economically and in a better yield in comparison with a known method. Therefore, this invention is a novel process for preparing cyclopentenone derivatives which is excellent industrially.

This invention will be further illustrated by the following non-limiting Examples in detail.

EXAMPLE 1

In a vertical tubular reaction vessel of 400 mm in length and 25 mm in inner-diameter a catalyst layer consisting of 5 g of boron phosphate which was obtained by concentrating a mixed aqueous solution of phosphoric acid and boron was placed and after the vessel was heated to a temperature of 350°C, 30 g of liquid $\gamma$-caprolactone was introduced into it at a rate of 6 g/hr while passing nitrogen gas at a rate of 4 l/hr. The results of quantitative analysis of 29.8 g of the product thus obtained by gas chromatography showed that 11.1 g of 2-methyl-2-cyclopentenone was obtained and 5.0 g in all of 2-methyl-4-cyclopentenone and 2-cyclohexenone and 5.8 g of unreacted $\gamma$-caprolactone were contained in it.

EXAMPLE 2

In the same reaction vessel as in Example 1 was placed a catalyst layer consisting of 5 g of silica-alumina (manufactured by Nikki Chemical Industry Co., Ltd., N-631 (L)) and after the vessel was heated to a temperature of 350°C, 50 g of liquid $\gamma$-methyl-$\epsilon$-acetoxycaproic acid at a rate of 6 g/hr was introduced into it while passing nitrogen gas at a rate of 4 l/hr. 46.2 g of the product thus obtained was rectified to give 20.0 g of 2,3-dimethyl-2-cyclopentenone and 2.8 g of 3-ethyl-2-cyclopentenone.

EXAMPLE 3

In the same reaction vessel as in Example 1 was placed a catalyst layer consisting of 5 g of solid phosphoric acid (manufactured by Nikki Chemical Industry Co., Ltd., N-501) and after the vessel was heated to a temperature of 400°C, 50 g of liquid $\gamma$-methyl-$\epsilon$-chlorocaproic acid was introduced into it at a rate of 5 g/hr while passing nitrogen gas at a rate of 5 l/hr. 40.0 g of the product obtained was rectified to afford 21.4 g of 2,3-dimethyl-2-cyclopentenone and 3.7 g of 3-ethyl-2-cyclopentenone.

EXAMPLE 4

By following the same procedure as in Example 1 except that 30 g of $\gamma$-methyl-$\epsilon$-hydroxycaproic acid was used as starting material in place of $\gamma$-caprolactone in Example 1, 29.0 g of the product was obtained and rectified to give 13.2 g of 2,3-dimethyl-2-cyclopentenone and 4.2 g of 3-ethyl-2-cyclopentenone.

EXAMPLE 5

By following the same procedure as in Example 2 except that 30 g of liquid $\gamma$-methyl-$\epsilon$-hydroxyheptanoic acid was used as starting material in place of $\gamma$-methyl-$\epsilon$-acetoxycaproic acid in Example 2, 28.0 g of the product was obtained and rectified to give 10.5 g of 2-ethyl-3-methyl-2-cyclopentenone.

EXAMPLE 6

By following the same procedure as in Example 3 except that 30 g of liquid $\gamma$-methyl-$\gamma$-methoxycaproic acid was used as starting material in place of $\gamma$-methyl-$\epsilon$-chlorocaproic acid in Example 3, 26.3 g of the product was obtained and rectified to afford 13.6 g of 2,3-dimethyl-2-cyclopentenone and 1.9 g of 3-ethyl-2-cyclopentenone.

EXAMPLE 7

By following the same procedure as in Example 3 except that 30 g of liquid $\gamma$-methyl-$\gamma$-bromopelargonic acid was used as starting material in place of $\gamma$-methyl-$\epsilon$-chlorocaproic acid in Example 3 and 4 g of 33 weight % nickel sulfate on silica gel was used, 29.5 g of the product was obtained and rectified to afford 6.1 g of 2-butyl-3-methyl-2-cyclopentenone.

EXAMPLE 8

By following the same procedure as in Example 1 except that 30 g of liquid $\gamma$-methyl-$\gamma$-pelargolactone was used as starting material in place of $\gamma$-caprolactone in Example 1 and 5 g of 40 weight % zinc sulfate on silica gel was used, 26.8 g of the product was obtained and rectified to give 5.1 g of 2-butyl-3-methyl-2-cyclopentenone.

EXAMPLE 9

By following the same procedure as in Example 1 except that 50 g of liquid $\gamma$-methyl-$\gamma$-decalactone was used as starting material at a rate of 9 g/hr in place of $\gamma$-caprolactone in Example 1, 49.0 g of the product was obtained and the results of quantitative analysis of it by gas chromatography showed that 41.0 g of 2-n-pentyl-3-methyl-2-cyclopentenone was obtained and 2.0 g of the unreacted $\gamma$-methyl-$\gamma$-decalactone was contained in it.

EXAMPLE 10

By following the same procedure as in Example 1 except that liquid $\gamma$-methyl-$\gamma$-caprolactone was used in place of $\gamma$-caprolactone in Example 1, 29.7 g of the product was obtained and the results of quantitative analysis of it by gas chromatography showed that 13.0 g of 2,3-dimethyl-2-cyclopentenone was obtained and 7.2 g of the unreacted $\gamma$-methyl-$\gamma$-caprolactone was contained in it.

EXAMPLE 11

By following the same procedure as in Example 1 except that 2.5 g of boron phosphate on 2.5 g of silica-gel was used as catalyst, 29.5 g of the product was obtained. The results of quantitative analysis of it by gas chromatography showed that 11.6 g of 2-methyl-2-cyclopentenone was obtained and 5.0 g of in all of 2-methyl-4-cyclopentenone and 2-cyclohexenone and 6.2 g of the unreacted γ-caprolactone were contained in it.

EXAMPLE 12

In the same reaction vessel as in Example 1 was placed a catalyst layer of 3.0 g of alumina-boria consisting of 0.4 g of boria on 2.6 g of alumina, and after the vessel was heated to a temperature of 400°C, 30 g of liquid γ-methyl-γ-chlorocapric acid was introduced into it at a rate of 6 g/hr under passing of nitrogen gas at a rate of 4 l/hr. 24.6 g of the product was obtained and rectified to afford 14.1 g of 2-n-pentyl-3-methyl-2-cyclopentenone and 2.4 g of 3-hexyl-2-cyclopentenone.

EXAMPLE 13

By following the same procedure as in Example 3 except that 30 g of liquid γ-caprolactone was used as starting material in place of γ-methyl-ε-chlorocaproic acid in Example 3, 29.5 g of the product was obtained and rectified to afford 12.1 of 2-methyl-2-cyclopentenone and 7.3 g in all of 2-methyl-4-cyclopentenone and 2-cyclohexenone.

EXAMPLE 14

By following the same procedure as in Example 2 except that 30 g of liquid γ-caprolactone was used as starting material in place of γ-methyl-ε-acetoxycaproic acid in Example 2, 29.0 g of the product was obtained and rectified to give 11.4 g of 2-methyl-2-cyclopentenone and 5.3 g in all of 2-methyl-4-cyclopentenone and 2-cyclohexenone.

EXAMPLE 15

By following the same procedure as in Example 12 except that 30 g of liquid γ-caprolactone was used as starting material in place of γ-methyl-γ-chlorocapric acid in Example 12, 29.2 g of the product was obtained and rectified to afford 12.7 g of 2-methyl-2-cyclopentenone and 4.8 g in all of 2-methyl-4-cyclopentenone and 2-cyclohexenone.

EXAMPLE 16

By following the same procedure as in Example 2 except that 50 g of liquid ε-methoxycaproic acid was used as starting material in place of γ-methyl-ε-acetoxycaproic acid in Example 2 and 5 g of boron phosphate was used as catalyst in place of silica-alumina, 46.5 g of the product was obtained and rectified to give 19.7 g of 2-methyl-2-cyclopentenone and 6.2 g in all of 2-methyl-4-cyclopentenone and 2-cyclohexenone.

EXAMPLE 17

By following the same procedure as in Example 16 except that 30 g of liquid γ-dimethyl-γ-butyrolactone was used in place of ε-methoxycaproic acid in Example 16 and the heating temperature was a temperature of 450°C, 29.5 g of the product was obtained and rectified to give 21.0 g of 3-methyl-2-cyclopentenone.

EXAMPLE 18

By following the same procedure as in Example 16 except that a solution of 30 g of γ,γ-undecamethylene-γ-butyrolactone in 30 g of benzene was used as starting material in place of ε-methoxycaproic acid in Example 16, 29.5 g of the product was obtained and rectified to afford 25.5 g of 13-keto-bicyclo-[10,3,0]-1(12)-pentadecene.

EXAMPLE 19

By following the same procedure as in Example 16 except that 50 g of liquid ε-caprolactone was used as starting material in place of ε-methoxycaproic acid in Example 16 and 5g of boron phosphate-chromium oxide whihc was prepared by adding and mixing 1 weight % of chromium oxide to the boron phosphate catalyst used in Example 1 was used, 48.3 g of the product was obtained and rectified to give 17.7 g of 2-methyl-2-cyclopentenone and 10.0 g in all of 2-methyl-4-cyclopentenone and 2-cyclohexenone.

EXAMPLE 20

By following the same procedure as in Example 19 except that 30 g of liquid γ-caprolactone was used as starting material in place of ε-caprolactone in Example 19 and the heating temperature was a temperatue of 300°C, 29.6 g of the product was obtained and rectified to give 14.4 g of 2-methyl-2-cyclopentenone and 6.2 g in all of 2-methyl-4-cyclopentenone and 2-cyclohexenone.

EXAMPLE 21

By following the same procedure as in Example 3 except that 30 g of γ-methyl-δ-valerolactone was used as starting material in place of γ-methyl-ε-chlorocaproic acid in Example 3, 29.2 g of the product was obtained and rectified to give 17.7 g of 3-methyl-2-cyclopentenone.

EXAMPLE 22

By following the same procedure as in Example 3 except that 30 g of liquid γ-valerolactone was used as starting material in place of γ-methyl-ε-chlorocaproic acid in Example 3, 29.0 g of the product was obtained and rectified to give 5.9 g of 2-cyclopentenone.

COMPARATIVE EXAMPLE 1

In 120 ml of 85% phosphoric acid was dissolved 200 g of phosphorus pentoxide and 22.8 g of γ-caprolactone was added to the solution. The mixture was heated with stirring at a temperature of 100°C for 3 hours and then poured into water and extracted with ether. 9.8 g of the product thus obtained was subjected to quanatitative analysis by gas chromatography and the results showed that 0.25 g of 2-methyl-2-cyclopentenone was obtained and 0.22 g in all of 2-methyl-4-cyclopentenone and 2-cyclohexenone and 8.0 g of the unreacted γ-caprolactone were contained in it.

What is claimed is:

1. A process for preparing a cyclopentanone derivative which comprises heating, in the gaseous state, a primary aliphatic acid containing from 5 to 13 carbon atoms and having a substituent selected from the group consisting of a halogen atom and a hydroxy, an alkoxy and an acyloxy radical in an γ-, δ- or ε-position or an intramolecular ester thereof in the presence of a solid acidic catalyst at a temperature of from 200°C. to 500°C., said catalyst being selected from the group consisting of silica-alumina, silica-magnesia, silica-boria, alumina-boria, silica-titania, sodium phosphate, calcium phosphate, magnesium phosphate, boron phosphate, zirconium phosphate, titanium phosphate, solid phosphoric acid, nickel sulfate, zinc sulfate, calcium sulfate, manganese sulfate, copper sulfate, cobalt sulfate, cadmium sulfate, strontium sulfate, magnesium sulfate, ferric sulfate, barium sulfate, potassium hydrogen sulfate, potassium sulfate, aluminum sulfate and chromium oxide, unsupported or supported on silica gel, alumina or diatomaceous earth.

2. A process as claimed in claim 1 in which the aliphatic acid or intramolecular ester is:
ε-methoxycaproic acid,
γ-methyl-ε-acetoxycaproic acid,
γ-methyl-ε-chlorocaproic acid,
γ-methyl-ε-hydroxycaproic acid,
γ-methyl-γ-methoxycaproic acid,
γ-methyl-ε-hydroxyheptanoic acid,
γ-methyl-γ-bromopelargonic acid,
γ-methyl-γ-chlorocapric acid,
γ-caprolactone,
γ-methyl-γ-caprolactone,
ε-caprolactone,
γ-dimethyl-γ-butyrolactone,
γ, 65-undecamethylene-γ-butyrolactone,
γ-valerolactone,
γ-methyl-δ-valerolactone,
γ-methyl-γ-decalactone, or
γ-methyl-γ-pelargolactone.

3. A process as claimed in claim 1 in which the following cyclopentenones are prepared:
2-cyclopentenone,
2-methyl-2-cyclopentenone,
2-methyl-4-cyclopentenone,
2,3-dimethyl-2-cyclopentenone,
3-ethyl-2-cyclopentenone,
2-ethyl-3-methyl-2-cyclopentenone,
2-butyl-3-methyl-2-cyclopentenone,
2-n-pentyl-3-methyl-2-cyclopentenone,
2-hexyl-2-cyclopentenone,
3-methyl-2-cyclopentenone, or
13-ketobicyclo[10,3,0]-1(12)-pentadecene.

4. A process as claimed in claim 1 in which the reaction is carried out at a temperature of from 300° to 450°C.

5. A process as claimed in claim 1, wherein the solid acidic catalyst is selected from the group consisting of silica-alumina, silica-magnesia, silica-boria and silica-titania.

6. A process as claimed in claim 5, wherein the temperature is from 300°C. to 450°C.

7. A process as claimed in claim 1, wherein the solid acidic catalyst is a metal sulfate unsupported or supported on silica gel, alumina, or diatomaceous earth.

8. A process as claimed in claim 7, wherein the temperature is from 300°C. to 450°C.

9. The process of claim 1, wherein the catalyst is boron phosphate.

10. The process of claim 1, wherein the catalyst is solid phosphoric acid.

* * * * *